United States Patent [19]

Schou

[11] 3,994,688
[45] Nov. 30, 1976

[54] METHOD AND REAGENT FOR QUANTITATIVE ANALYSIS OF L-LYSINE IN PROTEINACEOUS TEST SUBSTANCES

[75] Inventor: Jørgen Martin Dohm Schou, Vanlose, Denmark

[73] Assignee: A/S N. Foss Electric, Hillerod, Denmark

[22] Filed: Apr. 30, 1975

[21] Appl. No.: 573,215

[52] U.S. Cl............................ 23/230 M; 23/230 B; 260/279 R
[51] Int. Cl.² ................ G01N 33/02; C07D 219/00
[58] Field of Search...................... 23/230 M, 230 B; 260/279 R, 279 A

[56] References Cited
UNITED STATES PATENTS

| | | | |
|---|---|---|---|
| 3,539,574 | 11/1970 | Sheehan et al.................. | 260/279 R |
| 3,689,221 | 9/1972 | Udenfriend .................. | 23/230 M X |

OTHER PUBLICATIONS

Rapaport et al., J. Am. Chem. Soc., v. 94(9), pp. 3160–3167 (1972).

Primary Examiner—Morris O. Wolk
Assistant Examiner—Timothy W. Hagan
Attorney, Agent, or Firm—Ladas, Parry, Von Gehr, Goldsmith & Deschamps

[57] ABSTRACT

A test sample containing L-lysine in proteinaceous substances is reacted with a γ-formyl-pyridine reagent of the general formula

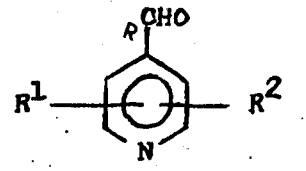

wherein $R^1$ and $R^2$ are each aliphatic carbon groups having not more than 4 carbon atoms or forming with two adjacent carbon atoms in the pyridine ring aromatic rings, in order to form the corresponding Schiff base, and the amount of reacted pyridine reagent is determined.

7 Claims, No Drawings

METHOD AND REAGENT FOR QUANTITATIVE ANALYSIS OF L-LYSINE IN PROTEINACEOUS TEST SUBSTANCES

The present invention relates to a method for quantitative analysis of L-lysine in proteinaceous test substances, more specifically materials of vegetable origin such as cereals, root crops, seeds and like materials; or animal origin, such as fish meal meat and bone meal. The invention further relates to a reagent for use in carrying out the method.

Biologically L-lysine(L-2,6-diamino-hexanoic acid) is an essential amino acid to humans and animals, i.e., the organism itself is unable or substantially unable to form the amount of L-lysine consumed in the metabolism and growth of the organism. The necessary amount of lysine therefore must be supplied to the organism either in free form or bonded in proteins from which it may be released by the digestive enzymes and thereafter be absorbed by the organism in biologically active form in sufficient amounts.

In feeding animals with one stomach, such as swine and poultry, lack of available lysine has proved to be the factor which frequently limits the growth rate of these species of animals. For this reason lysine is often referred to as "the first limiting amino acid".

Although it is not possible to render an inferior feed optimum with respect to nutritive value by adding lysine only, a substantial improvement is nearly always attainable.

There are a number of special reasons for lysine being the first limiting amino acid:

1. Many natural sources of protein have an inadequate lysine content, such as barley, wheat, rye, corn and rice.
2. The lysine may be present in proteins hard to digest, which means that it is only slowly and incompletely liberated from the protein.
3. Owing to the reactive $\epsilon$-amino group lysine is easily subject to derivation by reaction with other constituents of the source of protein. This will also reduce the accessible amount of lysine and with that the nutritive value.

Owing to the significance of lysine in the growth of animals with one stomach, it is of great import to be able to measure the amount of available lysine in feeds of various types.

The availability of lysine may correctly be determined by biological tests. These, however, are lengthy and costly to perform and therefore only have very limited use.

It is known to carry out chemical analyses to determine lysine and/or available lysine, and such analyses are less expensive and quicker to carry out than the biological tests. However, so far none of the known methods have become very popular as it is a question of rather impracticable laboratory methods taking one or two days.

The particular chemical conditions applying to the $\epsilon$-amino group of lysine are as follows:

1. The Maillard Reaction

If reducing types of sugar (glucose, lactose) are present in a source of protein, a spontaneous reaction will under certain conditions take place between the $\epsilon$-amino group of the lysine and the aldehyde group of the type of sugar involved. There is initially formed a Schiff base which is subsequently subject to an Amadori rearrangement to form an $N^\epsilon$-ketosyl lysine. This lysine derivative is biologically inert, and the organism is unable to regenerate lysine therefrom. It should be noted that the $\epsilon$-amino group also in the $N^\epsilon$-ketosyl lysine has basic properties.

2. Heating proteinaceous materials will produce a reaction between the $\epsilon$-amino group of the lysine and asparagine or glutamic side branches leading to formation of $\beta$-asparagyl and $\gamma$-glutamyl lysine. Due to the fact that the acylated $\epsilon$-amino group does not have basic properties, the compound cannot be released from the protein by the digestive enzymes, i.a. trypsin. It should be noted, however, that $\epsilon$-acylated lysine in the organism is extensively decomposable to form biologically active lysine.

A number of different methods for analysis of lysine are now known, each of which being, however, subject to substantial limitations and drawbacks.

Conventional amino acid analysis is carried out by subjecting a protein to hydrolysis with boiling strong hydrochloric acid for a prolonged period — 24 hours as a rule. The amino acids liberated in that process are separated by liquid chromatography, and the amount is determined colorimetrically after staining with ninhydrin.

In the acid hydrolysis the lysine derivatives present, if any, are broken down, in whole or in part, to form free lysine, and the quantitative analysis will therefore be expressive of "total lysine". In biological tests with certain materials it has not always been possible, however, to find the amounts of lysine corresponding to those ascertained by amino acid analysis. This has resulted in the term "availability" which therefore stands for the relative proportion of the total lysine being biologically active.

The availability of lysine in numerous materials is so variable that conventional amino acid analysis will only rarely provide a reliable evaluation of the amount of biologically active lysine.

The FDNB method — Carpenter method — has been developed specifically for measuring reactive lysine, i.e. the amount of lysine whose $\epsilon$-amino group has not been subject to derivation. The protein is reacted for a couple of hours with 1-fluoro-2,4-dinitrobenzene (FDNB) to convert the reactive lysine to $N^\epsilon$-(2,4-dinitrophenyl)lysine which is subsequently liberated by acid hydrolysis for 24 hours and then measured colorimetrically.

This method today is the most reliable for determination of reactive lysine (corresponding to available lysine), except for materials (cereals and seeds) having a high carbohydrate content which greatly affects the result of the analysis.

There are several versions of the FDNB method, but none of these offer any major advantages beyond those stated.

The DBC method, the dye-binding method, based on binding an acidic dye to the basic groups of a protein derived from lysine, arginine and histidine, may sometimes be employed for a quick evaluation of the amount of available lysine.

It has thus been substantiated that dye-binding does not take place with asparagyl and glutamyl lysine, though it does with ketosyl lysine. This means that the DBC method is used for determining the availability of lysine in materials where protein to protein reaction is predominant (fishmeal, meat-and-bone meal), but only poorly reflects reduced availability caused by protein and sugar reaction (milk powder).

These various factors lead to the conclusion that the ideal method for analysis of reactive lysine, serving as a basic for determining the amount of available lysine, should have the following characteristics:
1. The method must be quick and simple.
2. The effect of the other constituents of the test material must be suppressed.
3. The method specifically must be able to measure the amount of primary amino group deriving from protein-bonded lysine and which must be expected to represent the amount of biologically available lysine.

It is the object of the present invention to provide a method of analysis fulfilling the above criteria, which method comprises treating the test sample with an aldehyde reagent which owing to steric hindrance selectively reacts with free ε-amino groups of the lysine present in the test substance to form the corresponding Schiff base, whereupon the amount of reacted aldehyde reagent is determined.

What essentially complicates the analysis of protein in natural materials is that the latter have a high content of fat and carbohydrate. According to a preferred embodiment of the invention, the test material is therefore specially prepared such that the protein will be present in isolated state and prepared in a form rendering it reproducible and accessible to measuring. This may be accomplished by the test substance being subjected to extraction for isolating the digestive protein fraction and reacting the latter with an excess of the aldehyde reagent which owing to steric hindrance selectively reacts with free ε-amino groups in the lysine present in the test substance to form the corresponding Schiff base, whereupon the amount of reacted aldehyde reagent is determined by measuring the residual concentration of aldehyde reagent after the reaction.

In practice, this may be effected as follows:
The test material is ground while wet with an extraction liquid comprising equal parts of sodium hydroxide-sodium sulfite, solution and a solution of copper sulfate-ethylene glycol, preferably followed by centrifugation when the carbohydrate content is high. The blue-violet centrifugation material now contains the digestive proportion of protein as a copper complex — hence the intense violet color. The contents of fat and carbohydrate are negligible.

A particular problem arising when starch materials are treated with strong alkali is starch gelatinization. But owing the copper content of the extraction liquid, this phenomenon is found to absent, and therefore the said reagent has proved exceptionally suitable for selective isolation and preparation of the digestive protein fraction in a number of natural sources of protein having a high starch content.

The said isolation of protein takes in practice approx. 10 minutes.

A basic reaction in the lysine analysis has been selected the Schiff base formation between a primary amine (the ε-amino group of lysine) and an aldehyde. This reaction is normally quick and highly specific for a primary amine. However, also α-amino groups may react, and therefore the aldehyde should have steric hindrance so as to permit only a terminal amino group (the ε-amino group) to react with the aldehyde group.

Furthermore, it must be deemed advantageous that the aldehyde be water-soluble within a wide pH range, be measurable spectrophotometrically, be stable both as solids and in dissolved state and be obtainable in a pure state.

According to the present invention it has been found that these conditions are fulfilled when the aldehyde reagent employed is a substituted ε-formyl-pyridine derivative of the general formula:

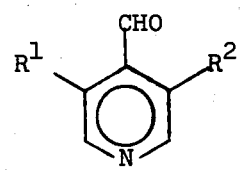

wherein $R^1$ and $R^2$ are each aliphatic carbon chains having not more than 4 carbon atoms or form together with the attached carbon atoms in the pyridine ring aromatic rings so as to form either a β-substituted quinoline or an acridine. Besides, the molecule should possibly contain groups to attain water solubility ($-SO_3H$) and increased or decreased reactivity ($Me_2N-$, $NO_2$).

Preferred compounds are:
9-formyl acridine (FA):

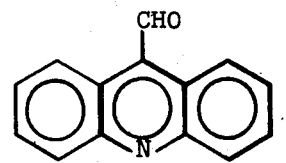

9-formyl-acridine-2-sulfonic acid (FAS):

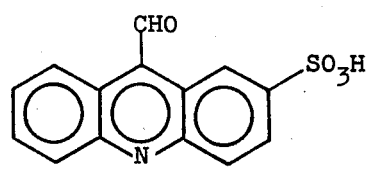

6-dimethylamino-9-formyl-acridine-2-sulfonic acid (DMA-FAS):

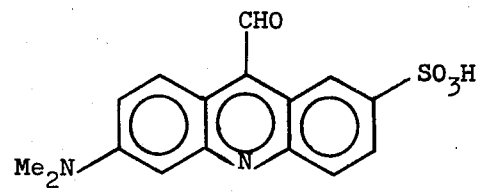

7-nitro-9-formyl-acridine-2-sulfonic acid (nitro-FAS):

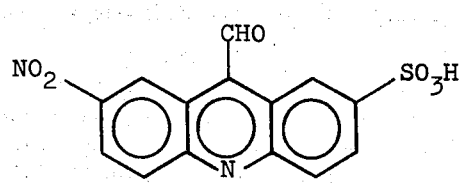

FA is known from the literature, whereas the other three are unknown. Of these, FAS has preference and has proved particularly suitable for analysis of lysine. In theory DMA-FAS will have higher reaction rate than FAS. Nitro-FAS must be expected to have slower reaction than FAS but is probably more selective and easier to measure owing to higher light absorption.

The below table specifies rate constants measured in the reaction of various aldehydes with the $\epsilon$-$NH_2$ group of the lysine.

TABLE
TABLE

Rate constants for the reaction
$RCHO + lysine -NH_2\ RCH = -lys + H_2O$

| Aldehyde | pH | $K \dfrac{mol}{l \cdot min.}$ | $K/k$ |
|---|---|---|---|
| 9-antracene aldehyde | 10,2 | 5,5 | ~20 |
| 9-antracene aldehyde | 13,0 | 8,0 | ~ 8 |
| 9-acridine aldehyde | 10,2 | 27 | 4 |
| 9-anthracene aldehyde, sulfonated | 10,2 | — | ~10 |
| 9-formyl-acridine-2-sulfonic acid | 9,2 | 40 | 1,5 |
| '' | 10,2 | 90 | ~ 4 |
| '' | 11,2 | 140 | ~10 |

The reagent 9-formyl-acridine-2-sulfonic acid offers the following advantages over the reagents used heretobefore for lysine analysis: It is specific with respect to the $\epsilon$-$NH_2$ group of the lysine, which means that the reaction with $\alpha$-$NH_2$ groups is decisively suppressed by the steric hindrance of the carbon skeleton of the aldehyde, and that derivatives of the type $\epsilon$-NH-R which may still be alkaline and thus subject to acylation of alkylation do not react at all.

The subject method of analysis may sometimes be applied direct to the untreated test substance if the latter contains only insignificant amounts of fat and carbohydrates. In the negative, it will be necessary to subject the test sample to a pretreatment wherein the proteins are isolated in the concentrated form.

Such a pretreatment is possible by treating the sample with a mixture of equal volumes of 0.2 m copper sulfate in 20% ethylene glycol and 1.0 m sodium hydroxide in 0.25 m sodium sulfite for 1–2 minutes. After centrifugation or filtration of the resultant suspension, the violet protein solution is isolated. This solution practically contains only the digestive protein proportion of the test material, starch, cellulose and fat being substantially insoluble in this reagent. It has been found that the extraction efficiency taken together with the digestiveness of the protein, determined by the pepsin-hydrochloric method, shows great correlation.

Based on the protein solution obtained above the lysine analysis is carried out as follows:

An aliquot is drawn from the solution and added to an excess of FAS solution. Reaction is carried out at a pH~11–12, followed by admixture of a minor excess of sodium borohydride dissolved. Add then sulfosalicylic acid solution to a pH<1 and filtrate or centrifugate. The residual concentration of reduced reagent is determined by spectrophotometric measuring. The consumption of FAS may be found be blind determination and with that the amount of reactive lysine in the test material.

The reagent 9-formyl-acridine-2-sulfonic acid is prepared as follows:

Based on 2-chlorobenzoic acid and aniline there is prepared N-phenylanthranilic acid which is ring closed and sulfonated with sulfuric acid to form acridone-2-sulfonic acid. By treating acridone-2-sulfonic acid with phosphoroxychloride followed by selective hydrolysis of the primarily formed 9-chloro-acridine2-sulfochloride there is obtained 9-chloro-acridine-2-sulfonic acid. By subsequent malonic ester synthesis there is prepared with 9-(diethylmalonyl)-acridine-2-sulfonic acid as intermediate 9-methyl-acridine-2-sulfonic acid.

This compound is condensed with p-nitrosodimethyl aniline to form sodium-9-(p-dimethyl-aminophenylazomethinyl)-acridine-2-sulfonate which by acid hydrolysis yields 9-formyl-acridine-2-sulfonic acid.

9-methyl-acridine-2-sulfonic acid is also prepared via condensation between o-amino-acetophenone and p-bromobenzene sulfamide yielding 9-methyl-acridine-2-sulfamide which by diazotization is converted to 9-methyl-acridine-2-sulfonic acid. The oxidation thereof to form aldehyde may also be effected by means of selenium dioxide.

The subject lysine analysis is illustrated below by means of some examples.

EXAMPLE 1

The following reagents are used in the analysis:
Reagent I:
49.94 g $CuSO_4$, $5H_2O$ in 800 ml $H_2O$ + 200 ml ethylene glycol
Reagent II:
40.00 g NaOH + 31.51 g $Na_2SO_3$ in 1000 ml $H_2O$
9-Formyl-acridine-2-sulfonic acid (FAS):
20.0 mMolar in 7.5% $Na_2HPO_4$ solution
$C_{14}H_9NO_4S$, $H_2O$; $m_w = 305.30$
Weigh out 1.2272 g FAS, dried for two hours at 100° C, fill up to 200 ml with 7.5% $Na_2HPO_4$.
7.5% $Na_2HPO_4$:
75 g $Na_2HPO_4$, $12H_2O$ in 1000 ml boiled out $H_2O$
Sodium borohydride ($NaBH_4$):
$m_w = 37.84$, 0.08 molar ~
305 mg in 100 ml N,N-dimethyl formamide
5-Sulfosalicylic acid (SSS):
$m_w$ dihydrate = 254.22, 0.75 molar ~
190.67 g in 1000 ml $H_2O$

Method

Weigh out a test batch corresponding to 0.35 ± 0.10 g protein in a small Foss-Let reactor cup. Add 12.5 ml reagent I + 12.5 ml reagent II. Place the cup in a Foss-Let reactor and allow reaction for 2 minutes. Transfer the suspension to a 50 ml centrifuge bottle and carry out centrifugation for 10 minutes at 10,000 rev.

Dispense by pipette 2.5 ml extraction + 2.5 ml FAS in a 50 ml

Erlenmeyer flask provided with a magnetic agitator; react for 20 minutes. Add 1 ml $NaBH_4$ solution and thereafter 20 ml SSS solution. Transfer to small centrifuge tubes and allow centrifugation for 5 minutes at 20,000 rev.

Measure the extinction of the above liquid in a spectro-photometer in an 0.5 mm flow cuvette.

Calculation

Blind determination = 2.5 ml regent I + III + 2.5 ml FAS and continue as analysis~$E_{bl}$.

$$\Sigma = \frac{E_{bl} \cdot 1000}{conc. \cdot mm} \text{concentration} = \frac{20 \cdot 2.5}{26} = 1.9231 \text{ milli-molar}$$

-continued $$\frac{bl - E}{\Sigma} = \text{mol/l}$$

$$\frac{(E_{bl} - E) \cdot 26}{\Sigma \cdot 1000} = \text{mol lysine/g sample}$$

$$\frac{(E_{bl} - E) \cdot 26 \cdot 10}{\Sigma \cdot 1000 \cdot a} = \text{mol lysine/g sample}$$

$$\frac{(E_{bl} - E) \cdot 26 \cdot 10 \cdot 100 \cdot 146}{\Sigma \cdot 1000 \cdot a} = \% \text{ lysine}$$

Abbreviated:

$$\frac{(E_{bl} - E) \, 26 \cdot 146}{\Sigma \cdot a} = \frac{(E_{bl} - E)}{\Sigma \cdot a} \, 3796 = \% \text{ lysine}$$

$26 = 2.5 + 2.5 + 1 + 20 \text{ ml}$ $146 = m_w$ of lysine

The above method of analysis is used for determination of lysine in various proteinaceous test subtances such as fishmeal, barley and meat-and-bone meal. For purposes of comparison similar analyses have been carried out with FDNB according to the Carpenter method. In samples having up to 10% lysine, a regression line of the following equation has been found:

% FAS lysine = 0.78 × % FDNB lysine + 0.18

$r = 0.98$
$S_d = 0.55$
$n = 62$

EXAMPLE 2

Use of 9-formyl acridine (FA) for analysis of lysine will appear from the following:

100 mg barley glutelin (2.97% available lysine) are treated for one hour with 10 ml 2 mM FA in 0.05 m triethylamine in 80% ethanol. After separation by centrifugation of the deposit the extinction of the above liquid is determined. By subtracting this value from the extinction value of the starting solution there is obtained the amount of extinction absorbed. Based thereon the amount of lysine present in the sample may be calculated.

In the test the lysine content was found to be 0.89%.

Other aldehydes (9-anthracene aldehyde, 2-methoxy-1-naphthaldehyde and 6-sulfo-2-methoxy-1-naphthaldehyde) will yield 0.28%, 0.07% and 0.07% respectively. Under identical conditions FAS will yield 2.05% lysine.

EXAMPLE 3

The following example described the synthesis of the reagent 9-formyl-acridine-2-sulfonic acid:

Step A — N-phenyl-anthranilic acid

Redistilled aniline (310 g, 3.32 mol), pure 2-chlorobenzoic acid (82 g, 0.52 mol), fresh dried potassium carbonate (82 g, 0.6 mol) and cupric oxide (2.0 g) are refluxed for two hours in an oil bath (air cooler). Excess aniline is initially removed by distillation in vacuum and later by water vapor. The remaining solution (500 ml) is boiled for 15 min. with 40 g of activated carbon and filtrated. The filtrate is poured into a mixture of concentrated hydrochloric acid (60 ml) and water (120 ml) during agitation. After cooling the deposit is separated by filtration, washed in water and dried at 120° C. This blue-grey product is cleaned out by dissolving 50 g in 1000 ml of water containing 25 g of sodium carbonate and boiling for 5 minutes with 25 g activated carbon. This is followed by filtration and precipitation with concentrated hydrochloric acid (vigorous foaming). The deposit is separated by filtration, washed in water and dried at 120° C.

Theoretical yield: 111 g
Yield in practice: 87 g of cream-colored powder
Relative yield: 78%

Step B — Acridone-2-sulfonic acid

N-phenyl-anthranilic acid (87 g) is treated at 100° C (water bath) with 1310 g of sulfuric acid ( ≧ 98%) for two hours. The deep-green solution is cooled and poured into 4 liters of water and 4 kg ice. After agitation for two hours the clear yellow deposit is separated by filtration and pressed onto the filter. The filter cake is rinsed with 5% hydrochloric acid and dried (100° C).

Theoretical yield: 117 g (monohydrate)
Yield in practice: 87 g of lemon-colored substance
Relative yield: 74%

Step C — 9-chloro-acridine-2-sulfonic acid

Acridone-2-sulfonic acid monohydrate (87 g) is treated with 260 ml of phosphoroxychloride (oil bath 130° C). This is refluxed for two hours after the solution becoming clear. Excess of phosphoroxychloride is removed by distillation in vacuum to obtain a viscous residue. After cooling this residue is dissolved in batches of 300 ml of chloroform until a total of approx. 1500 ml. These batches are gradually added to 2600 ml of 25% sodium carbonate solution and agitated for 30 minutes, after which the chloroform phase is separated. The upper layer is washed with additional 300 ml of chloroform which is combined with the major phase which is then filtrated. 41.5 ml of triethylamine are added to the clear chloroform phase together with 160 ml of acetone. This is followed by admixture of 450 ml of 1.0 m sodium hydroxide and agitation for two to three hours, while maintaining the temperature below 25° C. The lower phase is tested for unhydrolyzed material by an evaporation test and should leave at the most a colorless oily evaporation residue. The surface phase is separated, washed in 100 ml of chloroform and filtrated.

After cooling to 10° C there is quickly added half the volume of ice-cold concentrated hydrochloric acid, after which crystallization of a clear yellow substance takes place. After agitation for 30 min. precipitated material is separated by filtration, rinsed in one third of concentrated hydrochloric acid, ethanol (96%) and dry ethyl ether. Drying in desiccator over sodium hydroxide in vacuum.

Theoretical yield: 87 g
Yield in practice: 65 g of pure yellow substance
Relative yield: 75%

Step D — 9-(diethylmalonyl)-acridine-2-sulfonic acid 9-chloro-acridine-2-sulfonic acid (65 g, 0.225 mol) is added to a solution of sodium malonic ester in ethanol, prepared from 15.5 g of sodium (0.685 mol) dissolved in 350 ml of absolute ethanol and 101 ml of diethyl malonic ester. This is refluxed in an oil bath (85°–90° C) for 24 hours.

The deep-red solution is then cooled to room temperature, and during agitation 590 ml of 2 m hydrochloric acid are added. After agitation for one hour in cold water the deposit is separated by filtration, washed in water until the washing water shows turquoise fluorescence and dried at 100° C.

Theoretical yield: 93 g
Yield in practice: 86 g of clear yellow substance.
Relative yield: 92%

Step E — 9-methyl-acridine-2-sulfonic acid 9-(diethylmalonyl)-acridine-2-sulfonic acid (86 g) is suspended in 500 ml of half concentrated hydrochloric acid admixed with 25 ml of isoamyl alcohol and carefully heated to boiling (risk of excessive foaming) and refluxed for three hours. This is cooled during agitation in cold water and filtrated after 90 minutes. The deposit is washed in water and dried at 100° C.

Theoretical yield: 56 g
Yield in practice: 53 of sharply yellow substance
Relative yield: 95%

Step F — Sodium-9-(dimethylaminophenylazomethinyl)-acridine-2-sulfonate 9-methyl-acridine-2-sulfonic acid (53 g, 0.196 mol) is suspended in 400 ml of 96% ethanol, and 8.64 g of sodium hydroxide (1.10 equiv.) are added. This is sparingly refluxed for one hour to obtain a heavy crystal paste, and followed by light cooling and addition of 35.4 g (1.20 equiv.) of p-nitroso-dimethyl aniline which is washed down with as little ethanol as possible. Now reflux for six hours during vigorous agitation. As the crystal mass dissolves the color changes from green to brown and further to a deep red and after approx. 45 minutes profuse precipitation of the desired compound takes place (add a little additional ethanol if agitation is impossible).

After completed reaction the flask is left at 10° to 15° C during agitation for 15 hours (overnight). This is followed by separation by filtration of the precipitated compound which is washed on the filter with 2×60 ml of cold ethanol (used already for rinsing the reaction flask). Thorough suction is applied to the filter. Drying in incubator (80° C).

Theoretical yield: 83 g
Yield in practice: 68 g of bright red substance
Relative yield: 82%

Step G — 9-formyl-acridine-2-sulfonic acid (FAS)

Sodium-9-(p-dimethylaminophenylazomethinyl)-acridine-2-sulfonate (68 g) is dissolved in 700 ml of water, and 125 ml of concentrated hydrochloric acid are added. After 2 or 3 min. a yellow or yellowish brown crystalline substance is precipitated, and agitation is continued for 30 minutes. This is followed by filtration and the deposit is rinsed in 3×30 ml of 1 m hydrochloric acid and 2×30 ml of water. Drying in incubator (100° C).

The dry deposit (38.7 g) is suspended in 387 ml of water, and anhydrous sodium acetate (11,2 g) is added. Agitation is effected for 30 min. at <10° C, after which 7.7 g of activated carbon are added and agitation is continued for 15 min. Filtration is effected through a compact filter, and the deposit is rinsed in 3×50 ml of 0.5 m acetic acid. During agitation the filtrate is admixed with 54 ml of 5 m hydrochloric acid (half concentrated) whereby spontaneous precipitation of a lemon-colored crystalline material takes place. After agitation for 15 min. filtration is effected, followed by washing with 1 m of hydrochloric acid, water and finally with 96% ethyl alcohol. Drying at room temperature under vacuum.

Theoretical yield: 45 g of monohydrate
Yield in practice: 32 g of lemon-colored substance
Relative yield: 71%, 22% based on 2-chloro-benzoic acid.

Elementary analysis for $C_{14}H_{11}NO_5S$: Calculated: C, 55.08%; H, 3.63%; N, 4.59%; O, 26.20; S, 10.50%. Found: C, 55.28%; H, 3.68%; N, 4.70%; O, 26.01; S, 10.54%

| UV-absorption: | pH2: | $\lambda$ | = 361 nm |
| | | $\epsilon_{1cm}$ | = 54000 |
| | pH8: | $\lambda$ | = 362 nm |
| | | $\epsilon_{1cm}$ | = 28000 |
| | | $\lambda$ | = 375 nm (shoulder) |
| | | $\epsilon_{1cm}$ | = 26000 |

What is claimed is:

1. A method for quantitative analysis of biologically available L-lysin in proteinaceous substances, comprising the steps of reacting the protein with an aldehyde reagent comprising a substituted γ-formylpyridine derivative of the general formula:

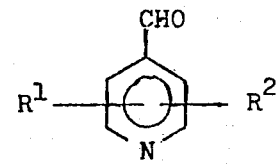

wherein $R^1$ and $R^2$ are each aliphatic carbon chains having not more than 4 carbon atoms or form together with two adjacent carbon atoms in the pyridine ring aromatic rings, in order to form the corresponding Schiff base, and determining the amount of reacted aldehyde reagent.

2. A method for quantitative analysis of biologically available L-lysine in proteinaceous substances, comprising the steps of isolating the digestive protein fraction by treating the test sample with an alkaline aqueous solution of a copper salt that will not dissolve fats and carbohydrates, reacting the isolated digestive protein fraction with an excess of an aldehyde reagent comprising a substituted γ-formylpyridine derivative of the general formula:

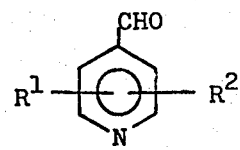

wherein $R^1$ and $R^2$ are each aliphatic carbon chains having not more than 4 carbon atoms or form together with two adjacent carbon atoms in the pyridine ring aromatic rings, in order to form the corresponding Schiff base, and determining the amount of reacted aldehyde reagent.

3. A method as claimed in claim 2, wherein the amount of reacted aldehyde reagent is determined by measuring the residual amount of aldehyde reagent after conclusion of the reaction.

4. A reagent for use in quantitative analysis of biologically available L-lysine in proteinaceous substances, comprising 9-formyl-acridine-2-sulfonic acid of the formula:

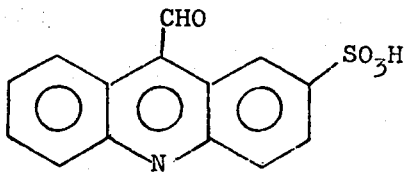

5. A reagent for use in quantitative analysis of biologically available L-lysine in proteinaceous substances, comprising 6-dimethyl-amino-9-formyl-acridine-2-sulfonic acid of the formula:

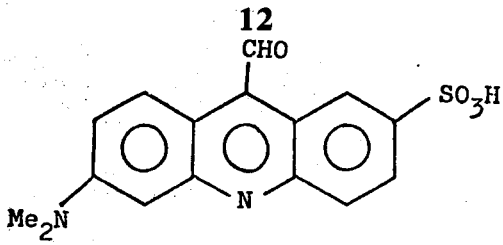

6. A reagent for use in quantitative analysis of biologically available L-lysine in proteinaceous substances, comprising 7-nitro-9-formyl-acridine-2-sulfonic acid of the formula:

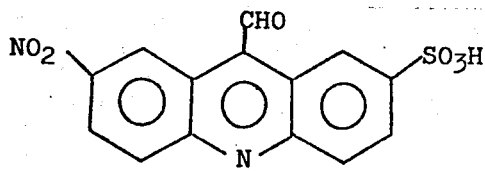

7. 9-formyl-acridine-2-sulfonic acid.

* * * * *